(12) United States Patent  
Miki (10) Patent No.: US 11,666,679 B2
(45) Date of Patent: Jun. 6, 2023

(54) FRAGRANCE ADJUSTMENT SYSTEM AND FRAGRANCE MATERIAL CARTRIDGE (71) Applicant: DAIKIN INDUSTRIES, LTD., Osaka (JP)

(72) Inventor: Sanae Miki, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 46 days.

(21) Appl. No.: 17/117,895

(22) Filed: Dec. 10, 2020

(65) Prior Publication Data

US 2021/0093742 A1 Apr. 1, 2021

Related U.S. Application Data

(63) Continuation of application No. PCT/JP2019/022991, filed on Jun. 10, 2019.

(30) Foreign Application Priority Data

Jun. 12, 2018 (JP) .............................. JP2018-112268

(51) Int. Cl.
| | |
|---|---|
| A61L 9/14 | (2006.01) |
| B05B 12/12 | (2006.01) |
| F24F 11/64 | (2018.01) |
| F24F 8/50 | (2021.01) |
| F24F 1/008 | (2019.01) |
| F24F 110/65 | (2018.01) |

(52) U.S. Cl.
CPC .............. *A61L 9/14* (2013.01); *B05B 12/12* (2013.01); *F24F 8/50* (2021.01); *F24F 11/64* (2018.01); *A61L 2209/11* (2013.01); *A61L 2209/111* (2013.01); *A61L 2209/134* (2013.01); *F24F 1/008* (2019.02); *F24F 2110/65* (2018.01)

(58) Field of Classification Search
None
See application file for complete search history.

(56) References Cited

FOREIGN PATENT DOCUMENTS

| | | |
|---|---|---|
| EP | 1 184 083 A1 | 3/2002 |
| JP | 3-3626 U | 1/1991 |
| JP | 3-236526 A | 10/1991 |
| JP | H03236526 A * | 10/1991 |
| JP | 4-268127 A | 9/1992 |
| JP | H04268127 A * | 9/1992 |
| JP | 5-215357 A | 8/1993 |
| JP | H05215357 A * | 8/1993 |
| JP | 11-278048 A | 10/1999 |
| JP | 2002-200157 A | 7/2002 |

(Continued)

OTHER PUBLICATIONS

Mariko et al. JPH04268127A—translated document (Year: 1992).*

(Continued)

*Primary Examiner* — Jelitza M Perez
(74) *Attorney, Agent, or Firm* — Global IP Counselors, LLP (57) ABSTRACT

A scent adjustment system includes a scent emitter arranged to supply a scent material to a target space, a storage, and a controller. The storage stores sensory information in which an intensity of a smell of the scent material perceived by a person and a concentration of the scent material are associated with each other. The controller adjusts the concentration of the scent material supplied from the scent emitter based on the sensory information stored in the storage.

4 Claims, 4 Drawing Sheets

(56) References Cited

FOREIGN PATENT DOCUMENTS

| | | | |
|---|---|---|---|
| JP | 2003-254927 A | | 9/2003 |
| JP | 2006174900 A | * | 7/2006 |
| JP | 2011-224071 A | | 11/2011 |

OTHER PUBLICATIONS

Akira et al. JPH03236526A—translated document (Year: 1991).*
Toshinori et al. JPH05215357A—translated document (Year: 1993).*
Inada, R. JP2006-174900A—translated document (Year: 2006).*
European Search Report of corresponding EP Application No. 19 81 9720.4 dated Jan. 20, 2022.
International Preliminary Report of corresponding PCT Application No. PCT/JP2019/022991 dated Dec. 24, 2020.
International Search Report of corresponding PCT Application No. PCT/JP2019/022991 dated Jul. 9, 2019.

* cited by examiner

FRAGRANCE ADJUSTMENT SYSTEM AND FRAGRANCE MATERIAL CARTRIDGE

CROSS-REFERENCE TO RELATED APPLICATIONS

This is a continuation of International Application No. PCT/JP2019/022991 filed on Jun. 10, 2019, which claims priority to Japanese Patent Application No. 2018-112268 filed on Jun. 12, 2018. The entire disclosures of these applications are incorporated by reference herein.

BACKGROUND

Field of Invention

The present disclosure relates to a scent adjustment system and a scent material cartridge.

Background Information

Japanese Unexamined Patent Publication No. H11-278048 discloses a supplier that supplies a scent material for a driver to a vehicle. The supplier supplies the scent material adjusted to have a predetermined concentration depending on the environment and the condition of the driver's body.

SUMMARY

In a first aspect, a scent adjustment system includes: a scent emitter that supplies a scent material to a target space; a storage that stores sensory information in which an intensity of a smell of the scent material perceived by a person and a concentration of the scent material are associated with each other; and a controller that adjusts a concentration of the scent material supplied from the scent emitter based on the sensory information stored in the storage.

DETAILED DESCRIPTION OF EMBODIMENT(S)

Figure 1:
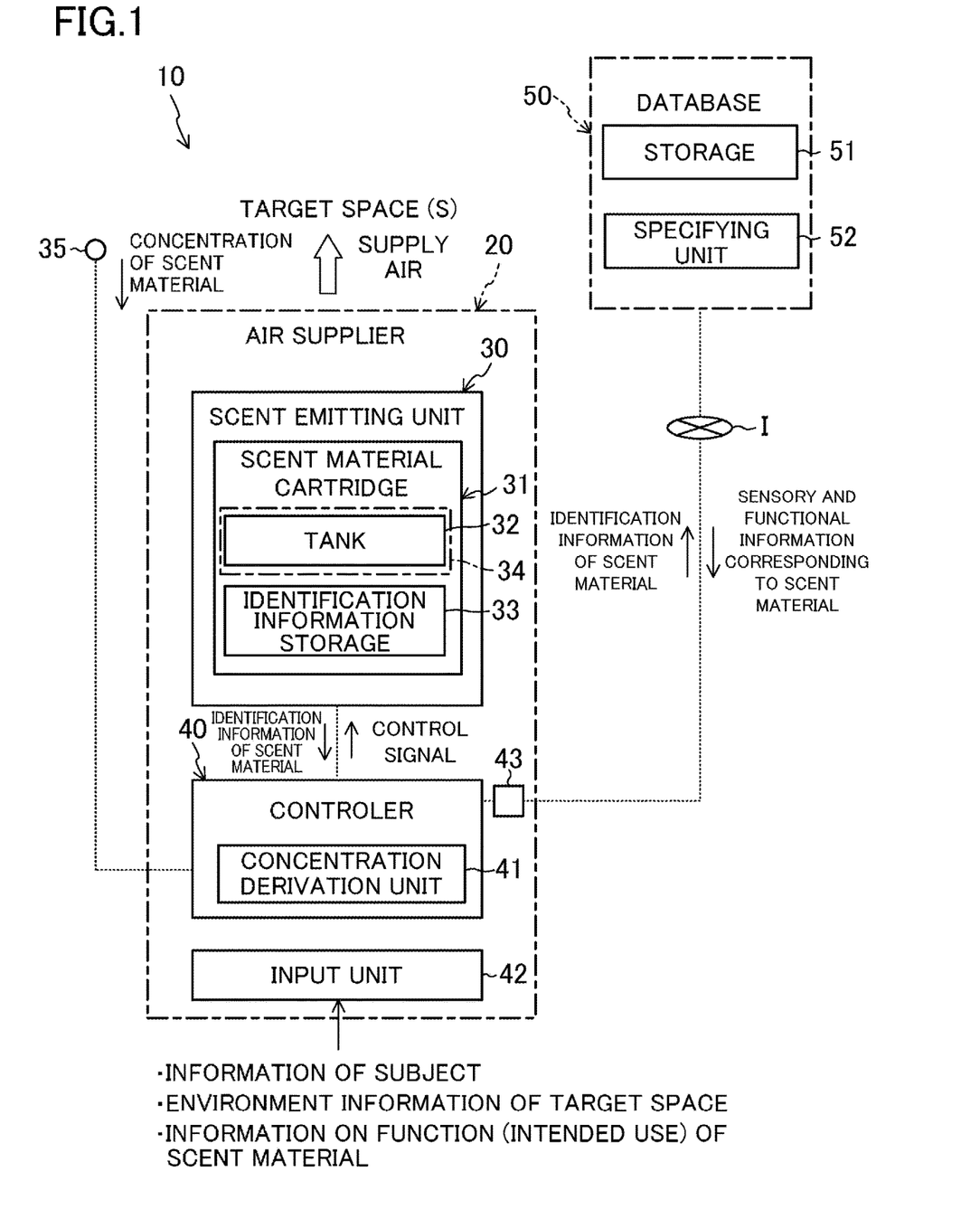
FIG. 1 is an overall schematic diagram illustrating a scent adjustment system of an embodiment.

A scent adjustment system (10) of the embodiment supplies air containing a scent material into a target space (S). The target space (S) is an indoor space such as a house or an office. As shown in FIG. 1, the scent adjustment system (10) of the present embodiment includes an air conditioner (20) that is an air supplier, a concentration sensor (35), and a database (50).

General Configuration of Air Conditioner

Figure 2:
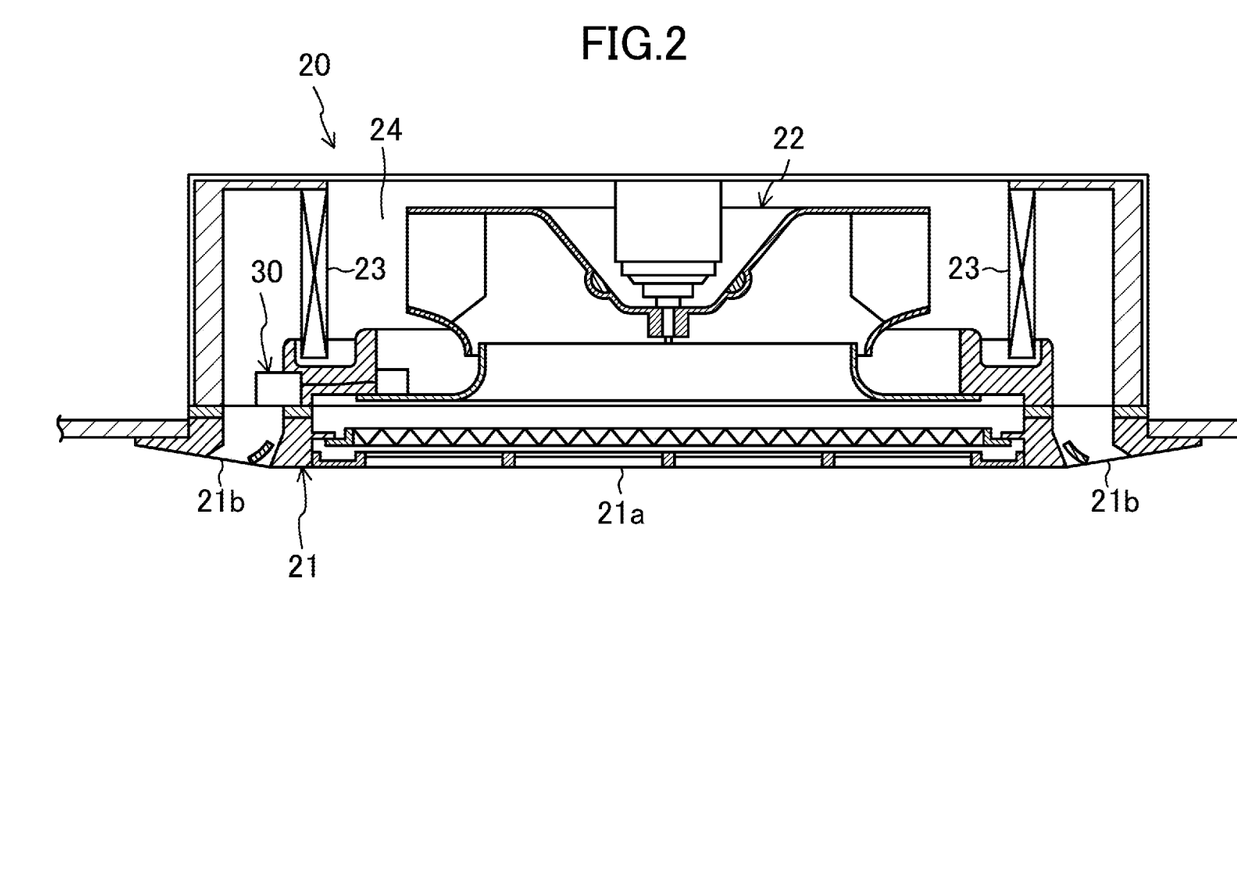
FIG. 2 is a schematic diagram illustrating an air conditioner of an embodiment.

The air conditioner (20) shown in FIG. 2 is mounted on the ceiling (strictly speaking, embedded in the ceiling). The air conditioner (20) may be of any other kind such as a ceiling hanging-type, a wall-hanging type, or a floor mounted-type. The air conditioner (20) includes a casing (21), a fan (22), and a heat exchanger (23).

The casing (21) includes an inlet (21a) (suction grille) at the center of its lower surface. The inlet (21a) on the lower surface of the casing (21) is surrounded by a plurality of outlets (21b). The casing (21) incorporates an air passage (24) extending from the inlet (21a) to the outlets (21b).

In the air passage (24), the fan (22) and the heat exchanger (23) are arranged in order from the upstream to the downstream. The heat exchanger (23) is connected to a refrigerant circuit (not shown) which circulates a refrigerant. The heat exchanger (23) functions as an evaporator or a condenser (radiator), depending on the direction of the refrigerant circulation. During a cooling operation of the air conditioner (20), the heat exchanger (23) serves as an evaporator to cool the refrigerant. During a heating operation of the air conditioner (20), the heat exchanger (23) serving as a condenser heats the refrigerant.

Scent Emitting Unit

The air conditioner (20) further includes a scent emitting unit (30) (scent emitter) that applies a scent material to supply air. As shown in FIG. 2, the scent emitting unit (30) is disposed downstream of the heat exchanger (23) in the air passage (24). The scent emitting unit (30) may also be disposed on the outflow end of the outlet (21b).

As shown in FIG. 1, the scent emitting unit (30) sprays the scent material contained in a tank (32) (reservoir) into the air through a nozzle. The scent emitting unit (30) may employ various spraying types, such as electrostatic spraying, ultrasonic spraying, steam spraying, centrifugal spraying, piezoelectric spraying, and two-fluid nozzle spraying.

The scent material cartridge (31) includes the tank (32) containing the scent material, and an identification information storage (33). The tank (32) is detachably attached to a detachable portion (34) of the scent emitting unit (30). The scent material is, for example, a liquid containing a scent component, and may further contain another component (e.g., ethanol) that is not a scent material, to dilute the scent component.

The identification information storage (33) is constituted by a memory device (e.g., a semiconductor memory). The identification information storage (33) stores identification information for specifying the kind of scent material to be contained in the tank (32). Specifically, the identification information storage (33) is capable of specifying the kind of scent material to be contained in the tank (32), using the identification information stored therein. The identification information of the identification information storage (33) is transferred to a specifying unit (52) in the database (50).

Controller

A controller (40) adjusts the concentration of the scent material supplied from the scent emitting unit (30) to the air. The controller (40) outputs a control signal for controlling the scent emitting unit (30) to the scent emitting unit (30). The controller (40) controls, for example, the amount and time of spraying the scent material supplied to the air passage (24) from the scent emitting unit (30) to adjust the concentration of the scent material. The controller (40) includes, for example, a control board, a processor (e.g., a micro-controller) mounted on the control board, and a memory device (e.g., a semiconductor memory) storing the software for actuating the processor.

The controller (40) includes a concentration derivation unit (41) that determines the optimal concentration of the scent material to be supplied to the target space (S). The concentration derivation unit (41) determines the optimal concentration of the scent material to be supplied to the target space (S) based on the information corresponding to the scent material (sensory information and functional information) transferred from the database (50) (the detail will be described later).

Complementary information used for controlling the scent emitting unit (30) is input to the input unit (42). The information may be output with, for example, a remote controller, external communication equipment (e.g., a smartphone, a personal computer), and a detector that detects and outputs the necessary information in real time and outputs the detected information. Examples of the information input to the input unit (42) include information of the subject, environment information of the target space, and information on the function of the scent material. Examples of the information of the subject include age, sex, and a woman's menstrual cycle. Examples of the environment information of the target space include the capacity of the target space and the number of people in the room. Examples of the functional information of the scent material may be defined as functional information (intended use) of the scent emitting unit desired by the user, such as a "desire to perform operation such that a quiet sleep inducing effect is obtained."

The air conditioner (20) further includes a communicator (43). The communicator (43) is constituted by, for example, a wireless LAN adapter, and is connected to the controller (40). The communicator (43) is connected to the database (50) on the server via, for example, a router and an Internet connection (I). This configuration makes it possible to exchange signals between the controller (40) and the database (50).

The communication line connecting the controller (40) and the database (50) may be partially or entirely wired. The database (50) may also be provided to, for example, the scent emitting unit (30) or the scent material cartridge (31).

Concentration Sensor

The concentration sensor (35) detects the concentration of the scent material supplied to the target space (S). The concentration sensor (35) may be disposed, for example, in the target space (S) or disposed downstream of the scent emitting unit (30) in the air passage (24).

Database

The database (50) includes a storage (51) and a specifying unit (52).

The storage (51) is a memory device (e.g., a semiconductor memory). The storage (51) stores information corresponding to a plurality or multiplicity of scent materials. Specifically, the information corresponding to the scent material includes sensory information in which at least the intensity of a smell of the scent material perceived by a person and the concentration of the scent material are associated. The information corresponding to the scent material also includes functional information in which the concentration and the function of the scent material are associated.

The "sensory information" is data concerning an olfactory sensibility of a person (i.e., the intensity of smell perceived by a person), and is previously determined for each scent material through experiments. The sensory information includes at least one of information of a detection threshold of the scent material, information of a discomfort concentration of the scent material, or information of an adaptive pattern to the scent material. The detection threshold may be defined as a minimum concentration at which a person perceives some smell. The discomfort concentration may be defined as a concentration at which the subject feels uncomfortable with the scent material. The adaptive pattern to the scent material may be defined as an olfactory sensibility which changes over time when the subject is exposed to the scent material.

In addition, the sensory information preferably includes at least one of information of the tendency of the olfactory sensibility depending on age, information of the tendency of the olfactory sensibility on sex, or information on the tendency of the olfactory sensibility depending on the woman's menstrual cycle. This is because the olfactory sensibility of a person changes depending on age, sex, and a woman's menstrual cycle.

This sensory information has a different characteristic depending on the kind of the scent material. Accordingly, the storage (51) stores various pieces of sensory information corresponding to each of the plurality of scent materials. The storage (51) appropriately accumulates sensory information of the scent material. Thus, the storage (51) has enough memory capacity to store sensory information corresponding to thousands of different scent materials.

The "functional information" is data concerning the influence of a predetermined function on the subject and is previously determined for each scent material through experiments. The functional information includes at least one of information on the concentration for exhibiting a predetermined function or information on safe exposure amount. The concentration for exhibiting a predetermined function may be defined as a concentration for achieving a sufficient function (efficacy) desired by the subject who is exposed to the scent material. If one scent material has a plurality of functions, the storage (51) stores concentrations for exhibiting the respective functions. The safe exposure amount may be defined as the maximum concentration at which the subject who is exposed to the scent material is not adversely affected.

The functional information may include information on the influence of an absorption pathway on the function. The pathway through which a person takes the scent material in includes, for example, the lungs and the skin. The optimal concentration for exhibiting the function changes depending on these pathways. When these absorption pathways are taken into consideration, a more optimal concentration at which the function is exhibited on the subject can be obtained.

This functional information has a different characteristic depending on the kind of the scent material. Accordingly, the storage (51) stores various pieces of functional information corresponding to the plurality of scent materials. The storage (51) appropriately accumulates functional information of the scent material. Thus, the storage (51) has enough memory capacity to store functional information corresponding to thousands of different scent materials.

The specifying unit (52) specifies the kind of the scent material used in the scent emitting unit (30). The specifying unit (52) specifies the scent material used in the scent emitting unit (30) based on the identification information stored in the identification information storage (33). More specifically, the identification information storage (33) of the scent material cartridge (31) stores identification information corresponding to the scent material (e.g., the scent material A) contained in the tank (32). The identification information is input to the database (50) via the communicator (43) and the Internet connection (I). The specifying unit (52) specifies the scent material contained in the tank (32) as, for example, a scent material A based on this identification information. The specifying unit (52) extracts the information (the sensory information and the functional information) corresponding to this scent material (scent material A) from the storage (51). The database (50) outputs the information of the scent material extracted in this manner to the controller (40).

Operation

The air conditioner (20) is configured to be capable of performing a scent material supply operation of supplying air containing a scent material to the target space (S), in addition to normal cooling and heating operations.

Overview of Scent Material Supply Operation

When the scent material supply operation starts, a fan (22) and a scent emitting unit (30) starts operating. In the air conditioner (20), the air in the target space (S) is sucked into an air passage (24) and then passes through a heat exchanger (23) and the scent emitting unit (30) in this order. In the scent emitting unit (30), the scent material contained in the tank (32) is sprayed into the air flowing through the air passage (24). The scent material that has been applied to the air in the air passage (24) is supplied to the target space (S).

Scent Material Concentration Adjustment Control

When the scent material supply operation starts, the identification information stored in the identification information storage (33) is input into the database (50) via the communicator (43) and the Internet connection (I). In the database (50), the specifying unit (52) extracts the information (sensory information and functional information) of the scent material corresponding to the identification information. The extracted information of the scent material is input into the controller (40) via the Internet connection (I) and the communicator (43). The controller (40) determines the optimal concentration of the scent material (target concentration (C*)) based on the input sensory information and functional information of the scent material. The concentration of the scent material detected by the concentration sensor (35) (detected concentration (C)) is input into the controller (40). The controller (40) controls the scent emitting unit (30) so that the detected concentration (C) reaches the target concentration (C*). This control adjusts the concentration of the scent material sprayed from the scent emitting unit (30) into the air, and allows the scent material at the target concentration (C*) to be applied to the target space (S).

Specific Example of Control

The controller (40) can acquire various kinds of sensory information and functional information from the database (50), and thus can perform various kinds of control depending on the intended use. One example of such control will now be described in detail.

Control in Consideration of Comfort

If priority is given to the comfort in the target space (S), the optimal concentration is determined using the detection threshold and the discomfort concentration in the sensory information corresponding to the scent material. Thus, the subject can certainly smell the scent material while avoiding from feeling uncomfortable due to an excessive concentration of the scent material. In such a control considering the comfort, the optimal concentration may be determined in consideration of the other sensory information and functional information.

Control in Consideration of Adaptive Pattern to Scent Material

It is also possible to perform a control in consideration of an adaptive pattern of the subject to the scent material. For example, the time of continuous scent material supply operation is measured to consider the adaptive pattern to the scent material according to this operation time. For example, with a certain scent material, the longer the operation time (strictly speaking, the time for which the subject is exposed to the scent material) is, the more the olfactory sensibility to the scent material decreases. Such an adaptive pattern is considered in order to determine the optimal concentration. In this example, the optimal concentration is gradually increased over operation time. This gradual increase allows the subject to feel comfort continuously.

Control in Consideration of Characteristics of Subject

Age, sex, a woman's menstrual cycle, and the like of the subject influence his/her sensibility to the scent material. For example, the subject inputs these pieces of information of the subject into the input unit (42). The controller (40) uses the information of the subject input into the input unit (42) and the sensory information stored in the storage (51) to determine the optimal concentration for the subject.

Control in Consideration of Environment Information

The concentration of the scent material in the air in the target space (S) changes depending on the capacity of the target space (S), the number of people in the target space (S), and other factors. For example, the subject inputs such environment information into the input unit (42). The controller (40) uses the environment information input into the input unit (42) to correct the optimal concentration.

Control to Exhibit Predetermined Function on Subject to

The subject inputs the desired function (intended use) into the input unit (42). The controller (40) determines the optimal concentration for exhibiting the input function (e.g., quiet sleep inducing effect) by using the functional information. In this determination, the safe exposure amount is also considered. This consideration allows avoidance of an adverse effect caused by an excessive concentration of the scent material on the subject, while the function desired by the subject is reliably exhibited.

Control in Consideration of Absorption Pathway

When the predetermined function is exhibited on the subject, the optimal concentration differs depending on an absorption pathway for the scent material. For example, the optimal concentration differs between the case in which a certain scent material is taken in via the lungs and the case in which a certain scent material is taken via the skin. Thus, the optimal concentration is calculated in consideration of such an absorption pathway.

Advantages of Embodiment

In the present embodiment, the scent material at the optimal concentration according to the intensity of smell perceived by a person is supplied to the target space (S) by using the sensory information of the scent material stored in the storage (51) of database (50).

The storage (51) stores the sensory information corresponding to the plurality of kinds of scent materials. Thus, even if the scent material used in the scent emitter (30) is changed, the sensory information corresponding to this scent material can be obtained. Accordingly, many scent materials are handled, and the scent material at the optimal concentration according to the intensity of the smell perceived by a person is supplied to the target space (S).

In the embodiment, the specifying unit (52) of the database (50) specifies the scent material used in the scent emitting unit (30). That is, the specifying unit (52) automatically extracts only the information corresponding to the scent material actually used from the information (sensory information and functional information) corresponding to the plurality of kinds of the scent materials. Specifically, the specifying unit (52) uses the identification information stored in the identification information storage (33) of the scent material cartridge (31), thereby allowing avoidance of discrepancy between the kind of the scent material actually sprayed and the kind of the scent material used for determination of the optimal concentration.

First Variation

Figure 3:
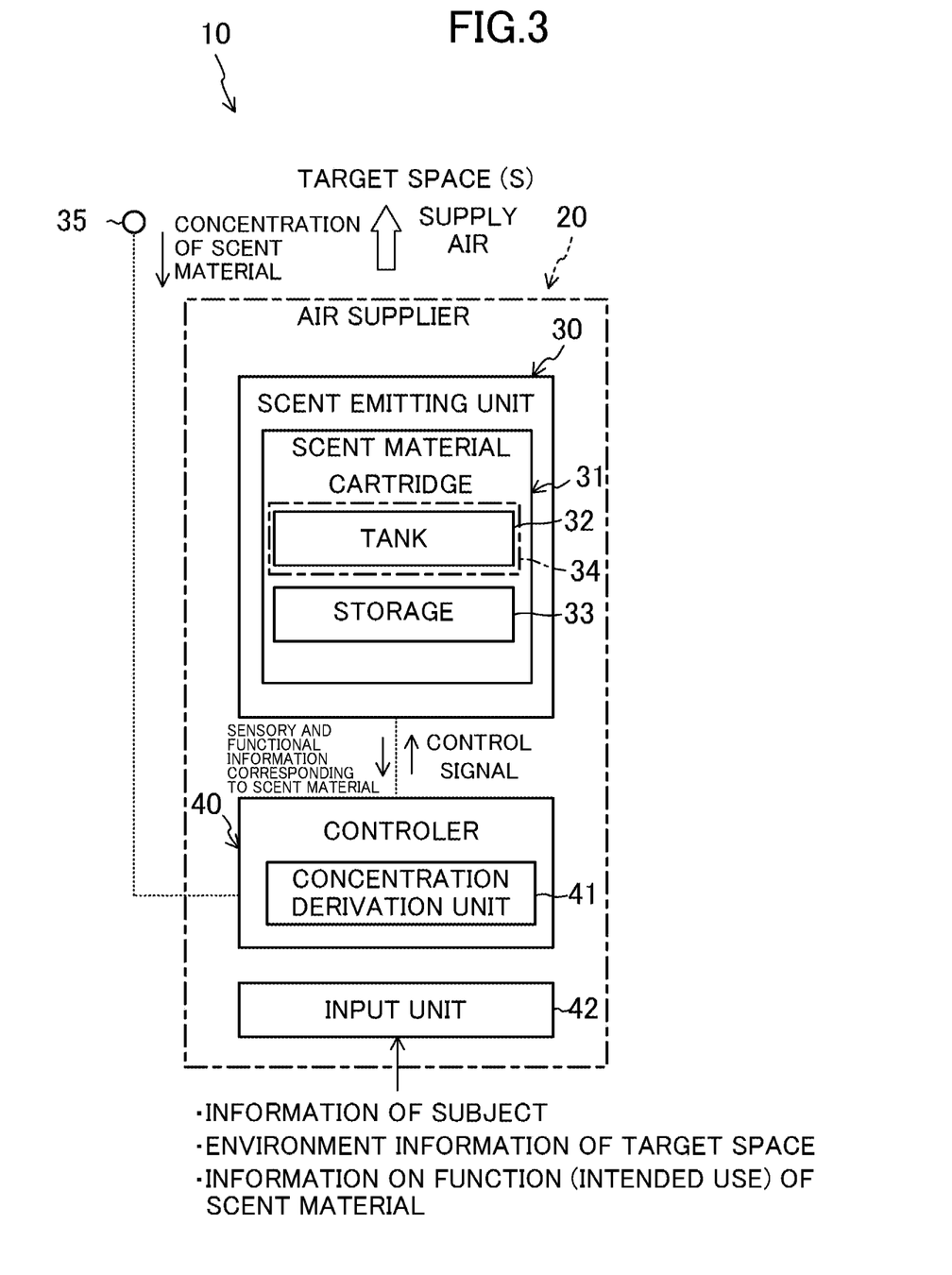
FIG. 3 is a diagram corresponding to FIG. 1 illustrating a scent adjustment system of a first variation.

A scent adjustment system (10) of the first variation shown in FIG. 3 has a different configuration from that of the embodiment. The scent adjustment system (10) of the first variation does not include the identification information storage (33), the communicator (43), and the database (50) of the embodiment. On the other hand, in the scent adjustment system (10) of the first variation, a scent material cartridge (31) includes a storage (51).

The storage (51) stores at least sensory information corresponding to the scent material contained in the tank (32). Specifically, for example, if the scent material contained in the tank (32) is a scent material A, the storage (51) stores at least the sensory information corresponding to the scent material A. As in the above embodiment, the storage (51) may store the functional information corresponding to the scent material A. The storage (51) of the first variation may store information corresponding to another scent material. However, the storage (51) stores preferably only information (sensory information and functional information) corresponding to the scent material contained in the tank (32). In this manner, the usage of the memory capacity of the storage (51) is kept minimum.

In the scent material supply operation of the first variation, the controller (40) stores the sensory information and the functional information stored in the storage (51) of the scent material cartridge (31). The controller (40) determines the optimal concentration of the scent material in the same manner as in the embodiment, based on this information.

In the first variation, an exchange of signals for controlling the scent emitting unit (30) is performed only inside the air conditioner (20). Thus, the communicator (43) of the embodiment and appliances such as a router are unnecessary. This configuration allows the scent adjustment system (10) to be simplified and allows the costs to be reduced.

The storage (51) stores information corresponding to the scent material cartridge (31), thereby allowing reliable avoidance of the discrepancy between the scent material actually used and the scent material corresponding to the information for determination of the optimal concentration.

Other advantages of the first variation are basically the same as those of the embodiment.

Second Variation

Figure 4:
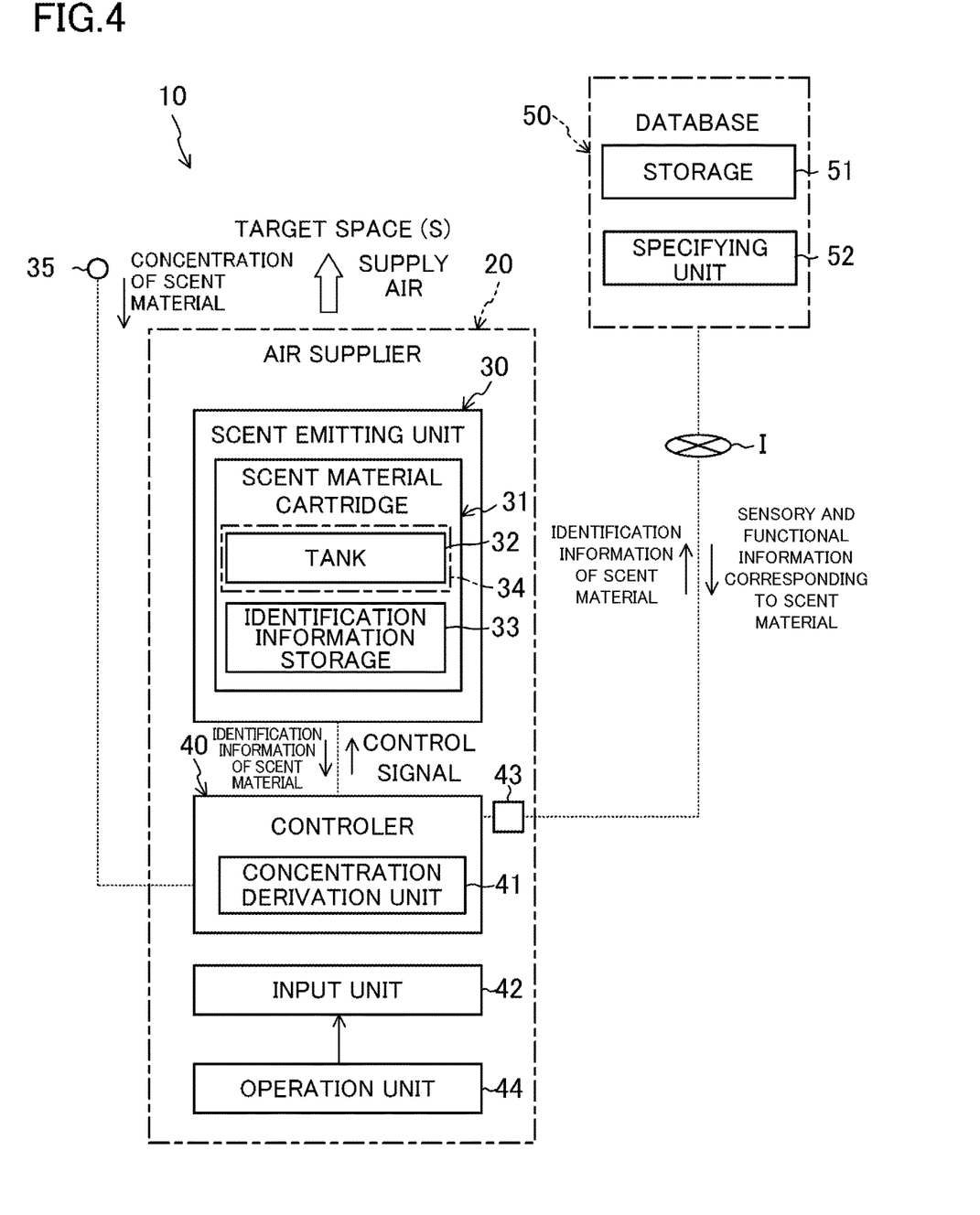
FIG. 4 is a diagram corresponding to FIG. 1 illustrating a scent adjustment system of a second variation.

A scent adjustment system (10) shown in FIG. 4 includes an operation unit (44) that adjusts a target concentration (C*) of the scent emitting unit (30). The operation unit (44) is a remote controller operated by a user. The user operates the operation unit (44) to appropriately change the concentration of the scent material supplied from the scent emitting unit (30) to the target space (S).

Specifically, the storage (51) stores the sensory information in which the intensity of a smell perceived by a person and the concentration of the scent material are associated with each other, for each kind of the scent material. More specifically, the storage (51) stores, for example, information in which the multiple-stage intensities of the smell and the multiple-stage concentrations of the scent material are associated with each other. The stages may include two or more stages, preferably two to seven stages, and more preferably five stages.

The operation unit (44) may change the intensity of the smell, for example, between one to five stages. When the operation unit (44) sets the intensity of the smell to "1," this signal is input to the input unit (42). Based on the sensory information stored in the storage (51), the concentration derivation unit (41) derives a concentration corresponding to the intensity of the smell of "1" and sets the concentration as the target concentration (C*). The controller (40) controls the scent emitting unit (30) so that the detected concentration (C) detected by the concentration sensor (35) reaches the target concentration (C*). Thus, the intensity of smell sprayed from the scent emitter (30) to the air is at the lowest level.

When the operation unit (44) sets the intensity of the smell to "5," this signal is input to the input unit (42). Based on the sensory information stored in the storage (51), the concentration derivation unit (41) derives a concentration corresponding to the intensity of the smell of "5" and sets the concentration as the target concentration (C*). The controller (40) controls the scent emitting unit (30) so that the detected concentration (C) detected by the concentration sensor (35) reaches the target concentration (C*). Thus, the intensity of smell sprayed from the scent emitter (30) to the air is at the highest level.

When the operation unit (44) sets the intensity of the smell to "3," this signal is input to the input unit (42). Based on the sensory information stored in the storage (51), the concentration derivation unit (41) derives a concentration corresponding to the intensity of the smell of "3" and sets the concentration as the target concentration (C*). The controller (40) controls the scent emitting unit (30) so that the detected concentration (C) detected by the concentration sensor (35) reaches the target concentration (C*). Thus, the intensity of smell sprayed from the scent emitter (30) to the air is at a middle level.

As described above, in the second variation, the intensity of the smell set by the operation unit (44) and the target concentration (C*) based on the sensory information stored in the storage (51) may be appropriately changed. This appropriate change allows the scent material having the intensity of the smell desired by the user to be applied to the target space (S).

As described above, the function (intended use) desired by the subject may be set by the operation unit (44) of the second variation. In this case, a signal relating to the function set by the operation unit (44) is input to the input unit (42). The controller (40) determines the optimal concentration (target concentration (C*)) for exhibiting the input function (e.g., quiet sleep inducing effect) by using the functional information. The controller (40) controls the scent emitting unit (30) so that the detected concentration (C) detected by the concentration sensor (35) reaches the target concentration (C*). This control allows the scent material at the optimal concentration for exhibiting the function desired by the user to be applied to the target space (S).

Third Variation

The third variation is configured such that in the scent adjustment system (10) of the second variation, when the detected concentration (C) detected by the concentration sensor (35) is equal to or higher than the discomfort concentration, the supply operation of supplying the scent material to the target space (S) stops.

Specifically, for example, when the operation unit (44) sets the intensity of the smell and performs an operation of turning ON the scent emitting unit (30), the scent material having a predetermined intensity of the smell is supplied to the target space (S). This operation will be referred to as a supply operation. During the supply operation, the concentration sensor (35) appropriately detects the concentration of the scent material in the air in the target space (S).

On the other hand, the storage (51) of the third variation stores the discomfort concentration as the sensory information corresponding to the scent material. The controller (40) stops the supply operation when the detected concentration (C) detected by the concentration sensor (35) is equal to or lower than the discomfort concentration stored in the storage (51). Accordingly, the supply of the scent material from the scent emitting unit (30) to the target space (S) ends immediately. Accordingly, the person in the target space (S) is avoided from feeling uncomfortable with the scent material, and is avoided from impairing the feeling of comfort.

Note that, the supply operation of the third variation may not change the intensity of smell to various stages as in the second variation, and the intensity of the smell of the scent material may be constant.

OTHER EMBODIMENTS

The above embodiment and variations may also be configured as follows.

The air supplier (20) of the embodiment is an air conditioner. However, the air supplier may have any configuration that supplies air to a target space (S), and includes, for example, an air purifier, a ventilator, a humidifier, and a dehumidifier.

While the embodiments and variations thereof have been described above, it will be understood that various changes in form and details may be made without departing from the spirit and scope of the claims. The embodiments and the variations thereof may be combined and replaced with each other without deteriorating intended functions of the present disclosure. The expressions of "first," "second," "third," described above are used to distinguish the words to which these expressions are given, and the number and order of the words are not limited.

As described above, the present disclosure is useful for a scent supplying system and a scent cartridge.

The invention claimed is:

1. A scent adjustment system comprising:
   a scent emitter arranged to supply a scent material to a target space;
   a storage that stores sensory information in which an intensity of a smell of the scent material perceived by a person and a concentration of the scent material are associated with each other, the sensory information further including information regarding a tendency of an olfactory sensibility with respect to the scent material depending on at least one human characteristic;
   an input unit to which information regarding a human characteristic is input; and
   a controller configured to adjust the concentration of the scent material supplied to the target space from the scent emitter based on the sensory information stored in the storage and the information on the human characteristics put to the input unit,
   the scent emitter including a scent material cartridge that includes a reservoir containing the scent material,
   the storage being provided in the scent material cartridge, and
   the sensory information stored in the storage corresponding to only the scent material contained in the reservoir of the scent material cartridge.

2. The scent adjustment system of claim 1, wherein the sensory information includes at least one of:
   a detection threshold for the scent material,
   a discomfort concentration of the scent material, and
   an adaptive pattern to the scent material.

3. The scent adjustment system of claim 1, wherein
   the storage further stores functional information in which a function and the concentration of the scent material are associated, and
   the controller is further configured to control the scent emitter based on the sensory information and the functional information stored in the storage.

4. The scent adjustment system of claim 2, further comprising:
   a concentration sensor arranged to detect the concentration of the scent material supplied to the target space,
   the sensory information includes a discomfort concentration of the scent material, and
   when the concentration detected by the concentration sensor is equal to or higher than the discomfort concentration during a supply operation of supplying the scent material to the target space by the scent emitter, the controller is configured to stop the supply operation of the scent emitter.

* * * * *